(12) United States Patent
Collins et al.

(10) Patent No.: US 8,338,659 B2
(45) Date of Patent: Dec. 25, 2012

(54) ABSORBENT ARTICLE FEATURING LEAKAGE WARNING

(75) Inventors: Meghan Elizabeth Collins, Palatine, IL (US); Richard Dickerson Mosbacher, Neenah, WI (US); Andrew Mark Long, Appleton, WI (US); Darold Dean Tippey, Brunswick, GA (US); Shirlee Ann Weber, Neenah, WI (US); Jessica Sara Van Handel, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1393 days.

(21) Appl. No.: 11/799,356

(22) Filed: Apr. 30, 2007

(65) Prior Publication Data

US 2008/0269703 A1    Oct. 30, 2008

(51) Int. Cl.
*A61F 13/42* (2006.01)
*A61F 13/20* (2006.01)
*A61F 13/22* (2006.01)
*A61F 13/34* (2006.01)
*A61F 13/475* (2006.01)
*A61F 13/47* (2006.01)

(52) U.S. Cl. ........ 604/361; 604/358; 604/367; 604/368; 604/378; 604/385.17; 604/385.18; 604/385.24

(58) Field of Classification Search .................. 604/358, 604/361, 367, 368, 378, 385.17, 385.18, 604/385.24
See application file for complete search history.

(56) References Cited

U.S. PATENT DOCUMENTS

| | | |
|---|---|---|
| 3,794,024 A | 2/1974 | Kokx et al. |
| 3,849,241 A | 11/1974 | Butin et al. |
| 4,289,794 A | 9/1981 | Kleiner et al. |
| 4,340,563 A | 7/1982 | Appel et al. |
| 4,405,297 A | 9/1983 | Appel et al. |
| 4,639,949 A | 2/1987 | Ales et al. |
| 4,699,823 A | 10/1987 | Kellenberger et al. |
| 4,704,116 A | 11/1987 | Enloe |
| 5,114,781 A | 5/1992 | Morman |
| 5,116,662 A | 5/1992 | Morman |
| 5,147,343 A | 9/1992 | Kellenberger |
| 5,266,592 A | 11/1993 | Grub et al. |
| 5,348,750 A | 9/1994 | Greenberg |
| 5,486,166 A | 1/1996 | Bishop et al. |
| 5,490,846 A | 2/1996 | Ellis et al. |
| 5,645,542 A | 7/1997 | Anjur et al. |
| 5,649,914 A | 7/1997 | Glaug et al. |
| 5,681,298 A | 10/1997 | Brunner et al. |

(Continued)

FOREIGN PATENT DOCUMENTS

EP          1 250 914 B1         5/2006

(Continued)

*Primary Examiner* — Leslie Deak
*Assistant Examiner* — Adam Marcetich
(74) *Attorney, Agent, or Firm* — Randall W. Fieldhack

(57) ABSTRACT

Disclosed is an absorbent article for preventing leakage, the article including an absorbent assembly having an absorbent assembly perimeter and a leakage warning element disposed adjacent a portion of the perimeter, wherein the leakage warning element is adapted to provide a physical sensation indicating a fullness level of the absorbent assembly. Also disclosed is an absorbent article for providing a wearer with a warning of potential leakage, the article including an absorbent assembly and a leakage warning element disposed adjacent the absorbent assembly, wherein the leakage warning element is adapted to impart a physical sensation to the wearer.

21 Claims, 6 Drawing Sheets

U.S. PATENT DOCUMENTS

| | | | |
|---|---|---|---|
| 5,702,376 | A | 12/1997 | Glaug et al. |
| 5,728,125 | A | 3/1998 | Salinas |
| 5,797,892 | A | 8/1998 | Glaug et al. |
| 5,883,028 | A | 3/1999 | Morman et al. |
| 5,904,671 | A | 5/1999 | Navot et al. |
| 5,964,743 | A | 10/1999 | Abuto et al. |
| 6,045,900 | A | 4/2000 | Haffner et al. |
| 6,231,557 | B1 | 5/2001 | Krautkramer et al. |
| 6,315,765 | B1 | 11/2001 | Datta et al. |
| 6,348,640 | B1 | 2/2002 | Navot et al. |
| 6,362,389 | B1 | 3/2002 | McDowall et al. |
| 6,387,084 | B1 | 5/2002 | VanGompel et al. |
| 6,506,958 | B2 | 1/2003 | Williams |
| 6,552,245 | B1 | 4/2003 | Roessler et al. |
| 6,576,810 | B1 * | 6/2003 | Underhill et al. ............ 604/361 |
| 6,596,919 | B2 | 7/2003 | Williams |
| 6,642,427 | B2 | 11/2003 | Roe et al. |
| 6,972,010 | B2 | 12/2005 | Pesce et al. |
| 7,002,055 | B2 | 2/2006 | Long et al. |
| 7,250,548 | B2 * | 7/2007 | Weber et al. ............... 604/361 |
| 2001/0049513 | A1 | 12/2001 | Neading et al. |
| 2003/0120227 | A1 * | 6/2003 | Williams ..................... 604/361 |
| 2003/0139291 | A1 | 7/2003 | Qin |
| 2004/0030310 | A1 | 2/2004 | Roe et al. |
| 2004/0064114 | A1 | 4/2004 | David et al. |
| 2004/0064116 | A1 | 4/2004 | Arora et al. |
| 2004/0081680 | A1 | 4/2004 | Pesce et al. |
| 2004/0128153 | A1 | 7/2004 | Zhang et al. |
| 2004/0254549 | A1 | 12/2004 | Olson et al. |
| 2004/0254550 | A1 | 12/2004 | Huang et al. |
| 2005/0124947 | A1 | 6/2005 | Fernfors |
| 2005/0137561 | A1 | 6/2005 | Mizutani et al. |
| 2006/0069363 | A1 | 3/2006 | Weber et al. |
| 2006/0105963 | A1 | 5/2006 | Yang et al. |
| 2006/0142713 | A1 | 6/2006 | Long et al. |
| 2006/0142714 | A1 | 6/2006 | Jackson et al. |
| 2006/0142715 | A1 | 6/2006 | Long et al. |
| 2006/0142716 | A1 | 6/2006 | Long et al. |
| 2006/0149197 | A1 | 7/2006 | Niemeyer |
| 2006/0247588 | A1 | 11/2006 | Olson et al. |
| 2007/0049883 | A1 | 3/2007 | Ales et al. |
| 2007/0088303 | A1 * | 4/2007 | Olson et al. ............ 604/385.01 |
| 2007/0149936 | A1 * | 6/2007 | Weber et al. ................ 604/361 |
| 2009/0157022 | A1 * | 6/2009 | MacDonald et al. ......... 604/361 |

FOREIGN PATENT DOCUMENTS

| | | |
|---|---|---|
| GB | 1 433 415 A | 4/1976 |
| WO | WO 01/95845 A1 | 12/2001 |
| WO | WO 03/002049 A1 | 1/2003 |
| WO | WO 03/051254 A2 | 6/2003 |
| WO | WO 2007/077538 A1 | 7/2007 |
| WO | WO 2008/020347 A1 | 2/2008 |

* cited by examiner

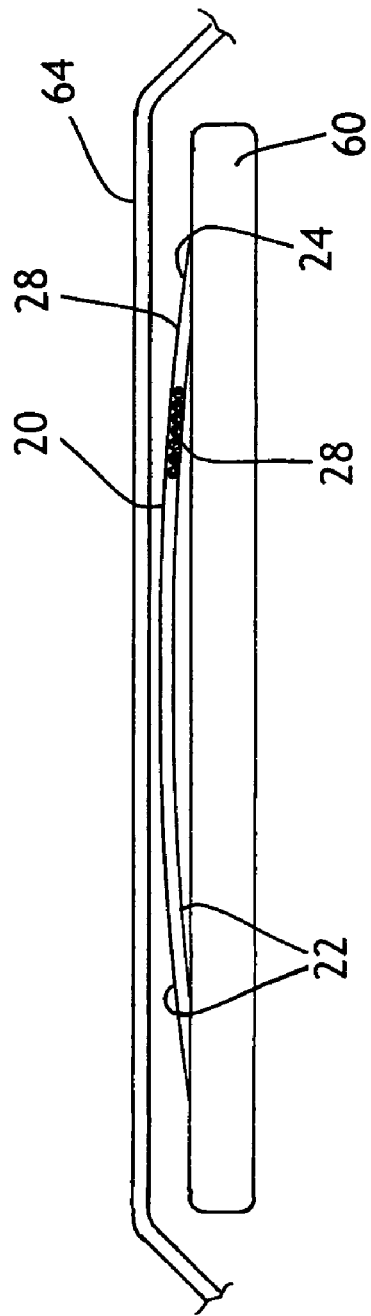
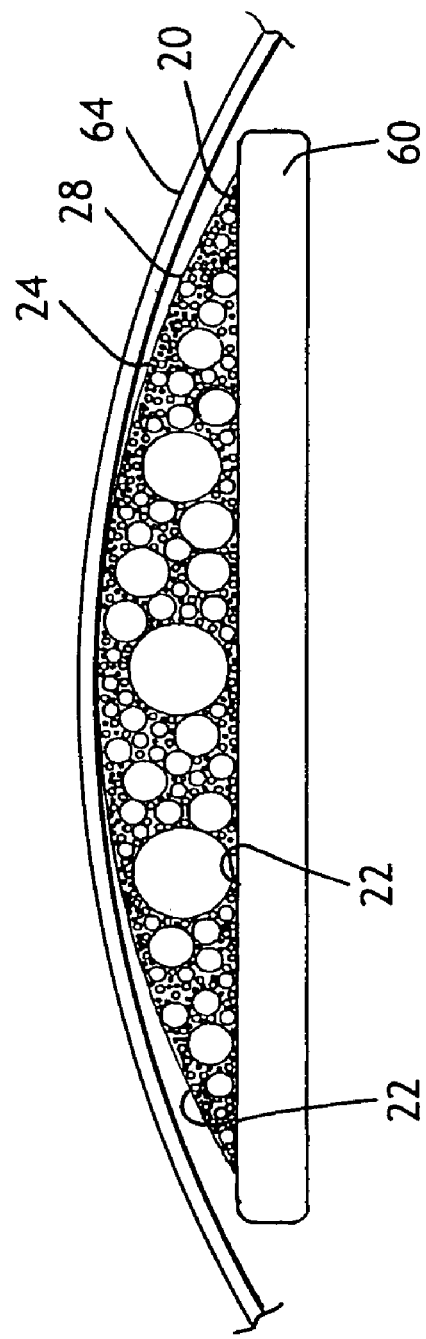

ABSORBENT ARTICLE FEATURING LEAKAGE WARNING

BACKGROUND

The present disclosure relates to absorbent articles that include a leakage warning element. More specifically, the disclosure relates to an absorbent article such as feminine care products, incontinence products, and training pants that provides the wearer with a noticeable physical sensation when the absorbent article is reaching fullness and prior to potential leakage from the absorbent article.

Absorbent articles such as feminine care products, incontinence products, and training pants are useful to absorb and contain body wastes. These products have developed to the extent that body exudates are quickly drawn and retained away from the wearer's skin so that the wearer remains relatively dry and comfortable. Although this improved performance enhances wearer dryness and comfort, it can reduce the wearer's ability to notice or recognize when the article is becoming full, especially if the wearer's attention is distracted by an activity. In one example, all adult care wearers, especially women, are very concerned about leakage in public. Some wearers may be so bothered by leakage that if it occurs in a public place, they will avoid that place and situation for the rest of their life. Leakage is therefore absolutely taboo in an adult care product. Similar circumstances can apply to feminine care products and training pants as well.

This application teaches products and methods to sense and inform an absorbent article wearer when leakage is about to occur so that the absorbent article wearer can reliably avoid leakage.

SUMMARY

In response to the discussed deficiencies in the prior art, a new absorbent article has been developed. Absorbent articles of the present disclosure provide a physical sensation upon contact with urine or other body exudates once the urine or other body exudates has nearly filled the absorbent article. As a result, the wearer will notice a distinct physical sensation to assist the wearer in recognizing when the absorbent article is nearing fullness.

In one aspect of the present disclosure, an absorbent article for preventing leakage includes an absorbent assembly having an absorbent assembly perimeter and a leakage warning element disposed adjacent a portion of the perimeter, wherein the leakage warning element is adapted to provide a physical sensation indicating a fullness level of the absorbent assembly.

In another aspect of the present disclosure, an absorbent article provides a wearer with a warning of potential leakage, the article including an absorbent assembly and a leakage warning element disposed adjacent the absorbent assembly, wherein the leakage warning element is adapted to impart a physical sensation to the wearer.

In another aspect of the present disclosure, absorbent article provides a wearer with a warning of potential leakage, the article including an absorbent assembly and a leakage warning element in fluid contact with the absorbent assembly, wherein the leakage warning element is adapted to impart a physical sensation to the wearer.

The purposes and features of the present disclosure will be set forth in the description that follows. Additional features of the disclosure may be realized and attained by the product and processes particularly pointed out in the written description and claims hereof, as well as from the appended drawings.

It is to be understood that both the foregoing general description and the following detailed description are exemplary and are intended to provide further explanation of the disclosure claimed. The accompanying drawings, which are incorporated in and constitute part of this specification, are included to illustrate and provide a further understanding of the disclosure.

BRIEF DESCRIPTION OF THE DRAWINGS

The present disclosure will be more fully understood, and further features will become apparent, when reference is made to the following detailed description and the accompanying drawings. The drawings are merely representative and are not intended to limit the scope of the claims.

FIG. 3 representatively illustrates a section view of a particular aspect of the leakage warning element in the aspect of a non-inflated container;

FIG. 4 representatively illustrates a section view of a particular aspect of a leakage warning element in the aspect of an inflated container;

Figure 1:
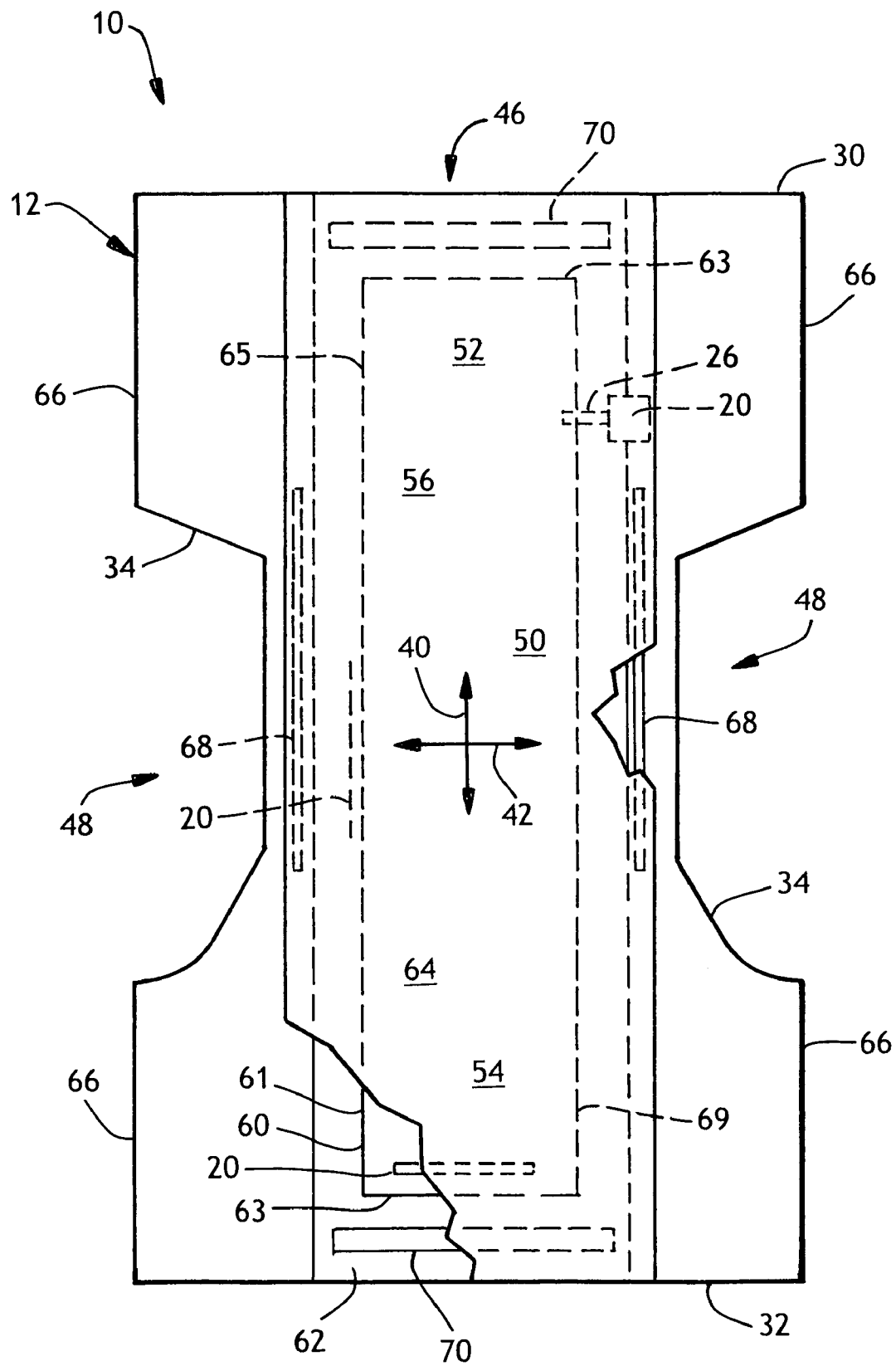
FIG. 1 representatively illustrates a plan view of a number of aspects of a pair of training pants showing the surface of the training pants that faces the wearer when worn, and with portions cut away to show underlying features.

Repeat use of reference characters in the present specification and drawings is intended to represent the same or analogous features or elements of the present disclosure. The drawings are representational and are not necessarily drawn to scale. Certain proportions thereof may be exaggerated, while others may be minimized.

Definitions

Within the context of this specification, each term or phrase below includes the following meaning or meanings:

"Attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end wearer.

"Bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

"Coform" refers to a blend of meltblown fibers and absorbent fibers such as cellulosic fibers that can be formed by air forming a meltblown polymer material while simultaneously blowing air-suspended fibers into the stream of meltblown fibers. The coform material may also include other materials, such as superabsorbent materials. The meltblown fibers and absorbent fibers are collected on a forming surface, such as provided by a foraminous belt. The forming surface may include a gas-pervious material that has been placed onto the forming surface.

"Connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements. "Connect" and its derivatives include permanent, releasable, or refastenable connection. In addition, the connecting can be completed either during the manufacturing process or by the end wearer.

"Disposable" refers to articles which are designed to be discarded after a limited use rather than being laundered or otherwise restored for reuse.

The terms "disposed on," "disposed along," "disposed with," or "disposed toward" and variations thereof are intended to mean that one element can be integral with another element, or that one element can be a separate structure bonded to or placed with or placed near another element.

"Elastic," "elasticized," "elasticity," and "elastomeric" mean that property of a material or composite by virtue of which it tends to recover its original size and shape after removal of a force causing a deformation. Suitably, an elastic material or composite can be elongated by at least 50 percent (to 150 percent) of its relaxed length and will recover, upon release of the applied force, at least 40 percent of its elongation.

"Extensible" refers to a material or composite which is capable of extension or deformation without breaking, but does not substantially recover its original size and shape after removal of a force causing the extension or deformation. Suitably, an extensible material or composite can be elongated by at least 50 percent (to 150 percent) of its relaxed length.

"Fiber" refers to a continuous or discontinuous member having a high ratio of length to diameter or width. Thus, a fiber may be a filament, a thread, a strand, a yarn, or any other member or combination of these members.

"Hydrophilic" describes fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, and fibers having contact angles greater than 90 degrees are designated "nonwettable" or hydrophobic.

"Join" and its derivatives refer to the connecting, adhering, bonding, attaching, sewing together, or the like, of two elements. Two elements will be considered to be joined together when they are integral with one another or joined directly to one another or indirectly to one another, such as when each is directly joined to intermediate elements. "Join" and its derivatives include permanent, releasable, or refastenable joinder. In addition, the joining can be completed either during the manufacturing process or by the end wearer.

"Layer" when used in the singular can have the dual meaning of a single element or a plurality of elements.

"Liquid impermeable," when used in describing a layer or multi-layer laminate means that liquid, such as urine, will not pass through the layer or laminate, under ordinary use conditions, in a direction generally perpendicular to the plane of the layer or laminate at the point of liquid contact.

"Liquid permeable" refers to any material that is not liquid impermeable.

"Meltblown" refers to fibers formed by extruding a molten thermoplastic material through a plurality of fine, usually circular, die capillaries as molten threads or filaments into converging high velocity gas (e.g., air) streams, generally heated, which attenuate the filaments of molten thermoplastic material to reduce their diameters. Such a process is disclosed, for example, in U.S. Pat. No. 3,849,241 to Butin et al. Meltblown fibers may be continuous or discontinuous and are generally self bonding when deposited onto a collecting surface.

"Member" when used in the singular can have the dual meaning of a single element or a plurality of elements.

"Nonwoven" and "nonwoven web" refer to materials and webs of material that are formed without the aid of a textile weaving or knitting process. For example, nonwoven materials, fabrics or webs have been formed from many processes such as, for example, meltblowing processes, spunbonding processes, air laying processes, and bonded carded web processes.

"Stretchable" means that a material can be stretched, without breaking, by at least 50 percent (to 150 percent of its initial (unstretched) length) in at least one direction. Elastic materials and extensible materials are each stretchable materials.

"Superabsorbent material" refers to a water-swellable, water-insoluble organic or inorganic material capable, under the most favorable conditions, of absorbing at least about ten times its weight and, more desirably, at least about thirty times its weight in an aqueous solution containing about 0.9 weight percent sodium chloride.

These terms may be defined with additional language in the remaining portions of the specification.

DETAILED DESCRIPTION

Figure 2:
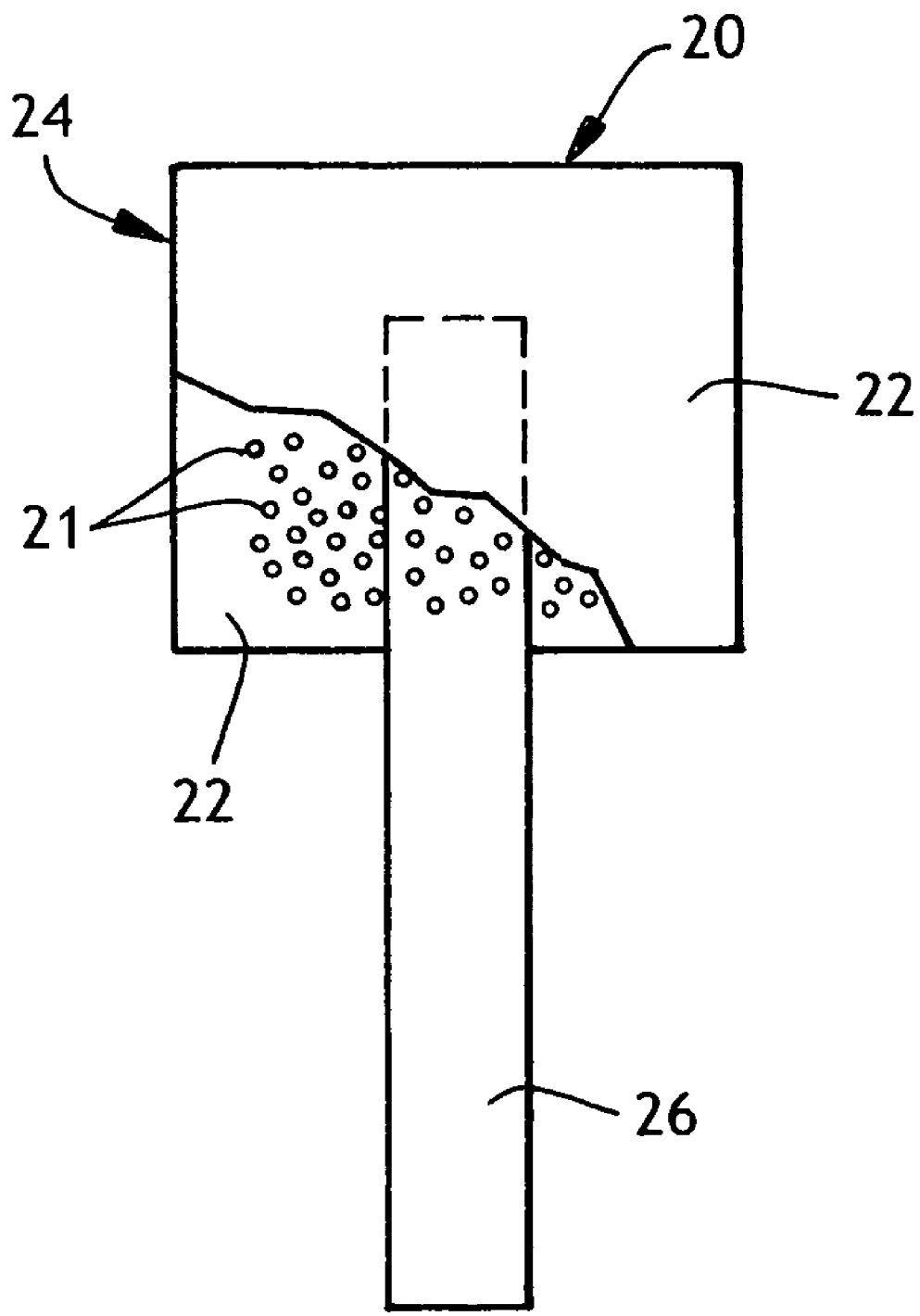
FIG. 2 representatively illustrates a plan view of a leakage warning element used in conjunction with the training pants of FIG. 1.

Referring now to the drawings and in particular to FIGS. 1 and 2, an absorbent article 10 of the present disclosure is representatively illustrated in the form of children's toilet training pants and is indicated, in its entirety by the reference numeral 12. Absorbent articles 10 of this type are described in more detail in U.S. Pat. No. 5,681,298 issue to Brunner et al., the contents of which are incorporated herein by reference to the extent that they are consistent (i.e., not in conflict) herewith. The absorbent article 10 includes a leakage warning element 20 that is adapted to create a distinct physical sensation to the wearer upon the absorbent article 10 nearing fullness, which can enhance a wearer's ability to recognize when leakage may be a threat.

While a leakage warning element 20 is illustrated in FIG. 1 with a disposable training pant 12, the leakage warning element 20 may also be used in conjunction with other garments. For example, a leakage warning element 20 of the disclosure may be used with other disposable absorbent articles such as diapers, diaper pants, incontinence articles, feminine pads, liners, and tampons, or the like. The descriptions of the various absorbent articles 10 described herein are for exemplary purposes only. Variations in the structures, materials, and designs of the absorbent articles 10 that do not impact the subject matter of this disclosure are possible and expected.

With reference to FIG. 1, an absorbent article 10 formed according to the disclosure is shown for purposes of illustration as a disposable training pant 12 for use by a child. The training pant 12 includes a leakage warning element 20 that is positioned and adapted to create a distinct physical sensation as the training pant 12 approaches fullness. Because the physical sensation is noticeable to the child, the child's ability to recognize when fullness is occurring will be enhanced. The training pant 12 will now be described in greater detail.

The training pant 12 is illustrated at an intermediate stage of assembly and in a flat and stretched condition in FIG. 1. The training pant 12 has opposite longitudinally spaced front and back end edges 30 and 32, and opposite side edges 34 extending between the end edges. The training pant 12 also defines longitudinal and transverse axes represented by arrows 40 and 42 in FIG. 1.

The finished training pant 12 becomes three-dimensional and thus defines a waist opening 46 and two leg openings 48 (FIG. 1). The finished training pant 12 has a crotch region 50 generally located between the leg openings 48. The crotch region 50 includes that portion of the training pant 12 which, when worn, is positioned between the legs of the wearer and covers the lower torso of the wearer. A front waist region 52 of the training pant 12 extends generally from the crotch region 50 to the front end edge 30, and a back waist region 54 extends from the crotch region 50 to the back end edge 32. In general, the longitudinal extent of the waist regions 50 and 52 is related to the distance between the end edges 30 and 32 of the training pant 12 and the crotch region 50, measured along the side edges 34. The training pant 12 also includes an inner surface 56 and an opposite outer surface (not shown).

With particular reference to FIGS. 1 and 2, the illustrated training pant 12 includes an absorbent assembly 60 sandwiched between an outercover 62 and a bodyside liner 64. The outercover 62 and liner 64 are desirably longer and wider than the absorbent assembly 60 and bonded together using adhesives, thermal bonds, ultrasonic bonds or other suitable means. Further, the absorbent assembly 60 is disposed on the outercover 62, and may be bonded directly thereto using adhesives, thermal bonds, ultrasonic bonds or other suitable means. The liner 64 may be bonded directly to the absorbent assembly 60 as well.

The outercover 62 may, for instance, include a single layer of film, a woven material, a nonwoven material or another suitable liquid permeable or liquid impermeable material. The outercover 62 may include a thin, substantially liquid impermeable web or sheet of plastic film such as polyethylene, polypropylene, polyvinyl chloride or similar material. Alternatively, the outercover 62 may include a nonwoven, fibrous web which has been suitably constructed and arranged to be substantially liquid impermeable. Still alternatively, the outercover 62 may include a layered or laminated material, such as a thermally bonded plastic film and nonwoven web composite or a stretch bonded laminate.

The outercover 62 may suitably include a material that is substantially liquid impermeable. The outercover 62 may be provided by a single layer of liquid impermeable material, or more suitably include a multi-layered laminate structure in which at least one of the layers is liquid impermeable. In particular aspects, the outer layer may suitably provide a relatively cloth-like texture to the wearer. A suitable liquid impermeable film for use as a liquid impermeable inner layer, or a single layer liquid impermeable outercover 62 is a 0.025 millimeter (1.0 mil) polyethylene film commercially available from Edison Plastics Company of South Plainfield, N.J., U.S.A. Alternatively, the outercover 62 may include a woven or non-woven fibrous web layer that has been totally or partially constructed or treated to impart the desired levels of liquid impermeability to selected regions that are adjacent or proximate the absorbent assembly.

The outercover 62 may also be stretchable, and in some aspects it may be elastomeric. For example, such an outercover material can include a 0.3 osy polypropylene spunbond that is necked 60 percent in the transverse direction 42 and creped 60 percent in the longitudinal direction 40, laminated with 3 grams per square meter (gsm) Bostik-Findley H2525A styrene-isoprene-styrene based adhesive to 8 gsm PEBAX 2533 film with 20 percent $TiO_2$ concentrate. Reference is made to U.S. Pat. No. 5,883,028, issued to Morman et al., U.S. Pat. No. 5,116,662 issued to Morman and U.S. Pat. No. 5,114,781 issued to Morman, all of which are hereby incorporated herein by reference to the extent that they are consistent (i.e., not in conflict) herewith, for additional information regarding suitable outercover materials.

The bodyside liner 64 may be any soft, flexible, porous sheet that passes liquids therethrough. The liner 64 may include, for example, a nonwoven web or sheet of wet strength tissue paper, a spunbonded, meltblown or bonded-carded web composed of synthetic polymer filaments, such as polypropylene, polyethylene, polyesters or the like, or a web of natural polymer filaments such as rayon or cotton. The liner 64 has a pore size that readily allows the passage therethrough of liquids, such as urine and other body exudates. The liner 64 may be selectively embossed or perforated with discrete slits or holes extending therethrough. Optionally, the web or sheet may be treated with a surfactant to aid in liquid transfer. One suitable liner material is a wettable spunbonded polypropylene web produced by the methods and apparatus described in U.S. Pat. No. 4,340,563 issued Jul. 20, 1982, and U.S. Pat. No. 4,405,297 issued Sep. 23, 1983, to Appel et al., the contents of which are incorporated herein by reference to the extent that they are consistent (i.e., not in conflict) herewith.

Alternatively, the bodyside liner 64 may also be stretchable, and in some aspects it may be elastomeric. For instance, the liner 64 can be a non-woven, spunbond polypropylene fabric composed of about 2 to 3 denier fibers formed into a web having a basis weight of about 12 gsm which is necked approximately 60 percent. Strands of about 9 gsm KRATON G2760 elastomer material placed eight strands per inch (2.54 cm) can be adhered to the necked spunbond material to impart elasticity to the spunbond fabric. The fabric can be surface treated with an operative amount of surfactant, such as about 0.6 percent AHCOVEL Base N62 surfactant, available from ICI Americas, a business having offices in Wilmington, Del., U.S.A. Other suitable materials may be extensible biaxially stretchable materials, such as a neck stretched/creped spunbond. Reference is made to U.S. Pat. No. 6,552,245, issued Apr. 22, 2003, to Roessler et al., the contents of which are incorporated herein by reference to the extent that they are consistent (i.e., not in conflict) herewith.

The absorbent assembly 60 can be in a variety of shapes and configurations as are known in the art, such as rectangular, hourglass shaped, I-shaped, and the like. The absorbent assembly 60 has opposed lateral edges 61 and opposed longitudinal ends 63. The lateral edges 61 and longitudinal ends 63 together make up the perimeter 65 of the absorbent assembly 60.

The absorbent assembly 60 may include various absorbent materials, such as an air-formed batt of cellulosic fibers (i.e., wood pulp fluff) or a coform material composed of a mixture of cellulosic fibers and synthetic polymer fibers. The absorbent assembly 60 may also include compounds to increase its absorbency, such as 0-95 weight percent of organic or inorganic high-absorbency materials, which are typically capable of absorbing at least about 15 and desirably more than 25 times their weight in water. Suitable high-absorbency materials are described in U.S. Pat. No. 4,699,823 issued Oct. 13, 1987, to Kellenberger et al. and U.S. Pat. No. 5,147,343 issued Sep. 15, 1992, to Kellenberger, the contents of which are incorporated herein by reference to the extent that they are consistent (i.e., not in conflict) herewith. High-absorbency materials are available from various commercial vendors, such as Dow Chemical Company, Hoechst Celanese Corporation, and Allied Colloids, Inc. The absorbent assembly 60 may also include tissue layers or acquisition or distribution layers to help maintain the integrity of fibrous absorbents or transport liquids (not shown).

The absorbent assembly 60 is suitably compressible, conformable, and capable of absorbing and retaining liquid body exudates released by the wearer. For example, the absorbent assembly can include a matrix of absorbent fibers, and more suitably cellulosic fluff, such as wood pulp fluff, and superabsorbent particles. One suitable pulp fluff is identified with the trade designation CR1654, commercially available from Bowater, Inc. of Greenville, S.C., U.S.A. As an alternative to wood pulp fluff, synthetic fibers, polymeric fibers, meltblown fibers, short cut homofil bicomponent synthetic fibers, or other natural fibers may be used. Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company of Midland, Mich., U.S.A., and Stockhausen Inc., Greensboro, N.C., U.S.A.

In one aspect, the absorbent assembly 60 may be stretchable so as not to inhibit the stretchability of other components to which the absorbent assembly may be adhered, such as the outercover 62 and/or the bodyside liner 64. For example, the absorbent assembly 60 may include materials disclosed in U.S. Pat. Nos. 5,964,743, 5,645,542, 6,231,557, 6,362,389, and international patent application WO 03/051254, the contents of which are incorporated herein by reference to the extent that they are consistent (i.e., not in conflict) herewith.

In some aspects, a surge management layer (not shown) may be included in the training pants 12. The surge management layer may be positioned in the training pants 12 in a variety of locations as is known in the art. For example, the surge management layer can be proximate the absorbent assembly 60, for example between the absorbent assembly 60 and the bodyside liner 64, and attached to one or more components of the training pants 12 by methods known in the art, such as by adhesive, ultrasonic or thermal bonding. In addition, the surge management layer may be positioned in the training pants 12 relative to the leakage warning element 20 in a variety of ways. For instance, the surge management layer may be disposed toward the liner 64 relative to the leakage warning element 20, or the surge management layer may be disposed toward the absorbent assembly 60 relative to the leakage warning element 20.

A surge management layer helps to decelerate and diffuse surges or gushes of liquid that may be rapidly introduced into the absorbent assembly 60. Desirably, the surge management layer can rapidly accept and temporarily hold the liquid prior to releasing the liquid into the storage or retention portions of the absorbent assembly 60. Examples of suitable surge management layers are described in U.S. Pat. No. 5,486,166 and U.S. Pat. No. 5,490,846, the contents of which are incorporated herein by reference to the extent that they are consistent (i.e., not in conflict) herewith.

The training pant 12 also includes a pair of side panels 66. Each side panel 66 is positioned transversely outward from the absorbent assembly 60 and bonded to the outercover 62, the bodyside liner 64, or both using adhesives, thermal bonds, ultrasonic bonds or other suitable means.

The side panels 66 are desirably formed of an elastic material capable of stretching in a direction parallel to the transverse axis 42 of the training pant 12. Further, the side panels 66 may also be formed of a gas permeable material, referred to as breathable material. The side panels 66 may, for instance, comprise a single layer of apertured film, a woven material, a nonwoven material or another suitable liquid permeable or liquid impermeable material. The side panels 66 may also comprise a laminate material, such as a stretch bonded laminate formed of a prestretched elastic meltblown inner layer sandwiched between and attached to a pair of spunbond polypropylene nonwoven webs having a basis weight of about 13.6 grams per square meter. Suitable elastic materials can be purchased from the Shell Chemical Company of Houston, Tex., U.S.A. under the tradename Kraton.

In one aspect, the side panels 66 are formed of a laminated material including a prestretched elastic meltblown inner layer having a basis weight of about 18 grams per square meter (gsm) sandwiched between and stretch bonded to a pair of spunbond webs each having a basis weight of about 14.9 gsm. The spunbond webs comprise bicomponent fibers formed of about 50 weight percent polypropylene and about 50 weight percent polyethylene in a side-by-side configuration. Alternately, suitable elastic strands may be substituted for the elastic meltblown layer.

The training pant 12 may also include leg elastic members 68 and waist elastic members 70 that are bonded to the outercover 62, the bodyside liner 64, or both to enhance fit and performance (FIG. 1). In particular, the leg elastic members 68 are operatively joined to the outercover 62 along each side edge 34 through the crotch region 50. Also, the waist elastic members 70 are operatively joined to the outercover 62 along the front and back end edges 30 and 32. The elastic members 68 and 70 may be bonded in place using adhesives, thermal bonds, ultrasonic bonds, stitching, or other suitable means. The elastic members 68 and 70 may be stretch bonded to the outercover 62, bonded in a relaxed state to a gathered portion of the outercover, or a combination of the two. One suitable method for attaching the elastic members 68 and 70 is disclosed in U.S. Pat. No. 4,639,949 issued Feb. 7, 1987, to Ales et al., the contents of which are incorporated herein by reference to the extent that they are consistent (i.e., not in conflict) herewith.

The training pant 12 may further include a pair of containment flaps (not shown) for inhibiting the lateral flow of body exudates. Containment flaps can be operatively attached to the training pant 12 in any suitable manner as is well known in the art. In particular, suitable constructions and arrangements for the containment flaps are generally well known to those skilled in the art and are described in U.S. Pat. No. 4,704,116 issued Nov. 3, 1987 to Enloe, the contents of which are incorporated herein by reference to the extent that they are consistent (i.e., not in conflict) herewith.

As noted previously, the leakage warning element 20 is positioned and adapted to create a distinct physical sensation upon the absorbent article 10 approaching fullness. As the absorbent assembly 60 fills with urine or other body exudates, the urine or other body exudates wicks into the leakage warning element 20 where the urine or other body exudates initiates a physical sensation that can be felt by the wearer of the absorbent article 10, thus alerting the wearer that a leak may soon occur.

As illustrated in FIG. 2, the leakage warning element 20 may include a substance that provides a physical sensation when the substance is contacted by urine or other body exudates, as is described in more detail below. That substance may be in the form of particles 21 captured between a pair of containment layers 22 or mixed into the absorbent assembly 60 or other material. The containment layers 22 form a container 24 to house and limit movement of the substance. Additional detail with respect to leakage warning element 20 is provided in U.S. Pat. No. 5,649,914 issued to Glaug et al.; in U.S. Pat. No. 5,681,298 issued to Brunner et al.; and in co-pending and co-assigned U.S. patent application Ser. No. 11/246,414, filed on Oct. 7, 2005 by Olson and titled "Absorbent Article Featuring a Temperature Change Member"; the contents of which are incorporated herein by reference to the extent that they are consistent (i.e., not in conflict) herewith.

In a number of aspects of the present disclosure illustrated in FIG. 1, the leakage warning element 20 is positioned within the training pant 12 so that urine or other body exudates filling the absorbent assembly 60 contacts the leakage warning element 20 prior to completely filling and eventually leaking from the training pant 12. Thus, the leakage warning element 20 is disposed with or near the absorbent assembly 60 so that urine or other body exudates contacting the absorbent assembly will also eventually contact the leakage warning element 20. Most desirably, the leakage warning element 20 is disposed on the bodyside of the absorbent assembly 60 so as to be sandwiched between the absorbent assembly 60 and the bodyside liner 64. In this way, the physical sensation resulting from the leakage warning element 20 is more easily noticed by the wearer. Generally, the closer to the perimeter 65 of the absorbent assembly 60 the leakage warning element 20 is placed, the less time a wearer will have to change the article 10 before a leak may occur. The remaining time available to a wearer is also dependent on other factors including the nature of the bodily waste captured in the absorbent assembly 60. For example, the rate of flow of menses in an absorbent assembly 60 is generally slower than the rate of flow of urine in an absorbent assembly 60.

Alternatively, however, the leakage warning element 20 may be located within the absorbent assembly 60 or beneath the absorbent assembly 60 (not shown). The leakage warning element 20 can also be positioned on the containment flaps or in any other suitable position in the training pant 12, as long as fluid communication is provided between the absorbent assembly 60 and the leakage warning element 20. In addition, leakage warning elements 20 may be positioned in more than one location within the training pant 12. The leakage warning element 20 may be bonded in position using adhesives, ultrasonic bonds, or other suitable means.

One or more leakage warning elements 20 may be disposed in the training pant 12. A pair of leakage warning elements 20 can be positioned on opposite sides of the longitudinal axis 40 and spaced apart from the intersection of the longitudinal and transverse axes 40, 42 along the transverse axis 42. Similarly, a pair of leakage warning elements 20 may be positioned on opposite sides of the transverse axis 42 and spaced apart from the intersection of the longitudinal and transverse axes 40, 42 along the longitudinal axis 40. In another aspect, leakage warning elements 20 may be positioned at each of the points at which an axis meets the perimeter 65 of the absorbent assembly 60. In still another aspect, the leakage warning elements 20 may be positioned completely or partially along the entire absorbent assembly perimeter 65.

The position and/or structure of the leakage warning elements 20 should be such that the leakage warning elements 20 come in contact with urine or other bodily waste as the absorbent assembly 60 fills but prior to any leakage from the absorbent assembly 60. The leakage warning elements 20 may be centered in the longitudinal direction 40. Alternatively, however, the leakage warning elements 20 may be located off the transverse axis 40 of the training pant 12. Likewise, the leakage warning elements 20 may be centered in the transverse direction 42 or may be located off the longitudinal axis 42 of the training pant 12.

As illustrated in FIG. 1, the leakage warning element 20 may be positioned in the front 50 percent of the training pant 12. Because the training pant 12 is most likely to be in contact with the wearer in the region of the wearer's abdomen, the leakage warning elements 20 are desirably positioned in the front waist region 52 and more particularly in the front one-third of the length of the training pant 12. Alternatively, leakage warning elements 20 may be positioned in the back waist region 54, such as in the back one-third of the length of the training pant 12.

In other aspects of the present disclosure illustrated in FIGS. 1 and 2, the leakage warning elements 20 may be positioned such that they are spaced apart from the absorbent assembly 60. For example, the leakage warning elements 20 may be positioned between the liner 64 and the outercover 62, but separated from the absorbent assembly 60. In such an arrangement, accommodation can be made to ensure urine or other bodily waste is transported from the absorbent assembly 60 to the leakage warning elements 20. Such transport may be accomplished with the liner 64 or with a separate transport member 26. The transport member 26 is useful to transport liquid deposited in the absorbent assembly to the leakage warning elements 20. The transport member 26 has one end positioned in the container 24 in contact with the leakage warning elements 20 and an opposite end that is positioned outside the container 24 and in contact with the absorbent assembly 60. By way of illustration, the transport member 26 may be rectangular and have a width of about 1 cm (0.4 in) and a length of about 5 cm (2 in).

The transport member 26 is formed of a material and/or treated to transport urine in the plane of the transport member. The transport member 26 may be formed of a web of natural or synthetic fibers. Specific fibers for use in forming such a web include rayon sliver, particularly those having a trilobal geometry, sulfonated pulp, hot calendered pulp, or the like.

The leakage warning element 20 may be constructed so that urine or other body exudates either enters the container 24 directly through the containment layers 22, is transported into the container 24 by the transport member 26, or both. Where urine or other body exudates is transported into the container 24, for example, the containment layers 22 may include a liquid impermeable material, such as a liquid impermeable film, a liquid impermeable nonwoven web, or the like.

The size and shape of the leakage warning element 20 may vary widely. For example, an individual leakage warning element 20 may be rectangular and measure about 4 cm. (1.6 in) by about 7 cm. (2.8 in). Alternatively, the leakage warning element 20 may be in the form of strips (not shown) that extend over the full length or width of the training pant 12.

In use, the leakage warning element 20 in the training pant 12 is designed to draw the wearer's attention to the fact that the absorbent assembly 60 is nearing fullness. The leakage warning element 20 is placed within the training pant 12 so that urine or other body exudates enters the container 24 directly through the containment layers 22, is transported into the container by the transport member 26, or both. By either or both methods, urine or other body exudates will come into contact with the leakage warning element 20. Depending on the particular type of leakage warning element 20 used, the leakage warning element 20 will produce a physical sensation. As a result, the wearer will experience that physical sensation when the absorbent assembly 60 is approaching fullness to indicate to the wearer that potential leakage is imminent.

As noted previously, the leakage warning element 20 is positioned and adapted to create a distinct physical sensation upon the absorbent article 10 approaching fullness. The physical sensation may be a temperature change such as cooling or heating, may be a pressure change such as from an expandable element, or may be a foaming, fizzing, bubbling, or other physical sensation.

A physical sensation in the form of a temperature change can result from a temperature change substance that, in the aspect of FIGS. 1 and 2, is in the form of particles 21 captured between the pair of containment layers 22. The containment layers 22 form the container 24 to house and limit movement of the temperature change substance. As described above, the leakage warning element 20 may also include a transport member 26 for transporting liquid into the container 24.

The temperature change substance includes a material that provides a temperature change when placed near the wearer and contacted with urine. The temperature change can be either an absorption or release of heat to change the temperature of the surroundings to a point noticeable to the wearer. An absorption of heat by the temperature change substance will provide the wearer with a cool sensation, while a release of heat by the substance will provide the wearer with a warm sensation.

The temperature change substance is responsive to contact with an aqueous solution such as urine to either absorb or release heat. The mechanism by which this is accomplished is the dissolution of the substance in the aqueous solution, the swelling of the substance in the aqueous solution, or the reaction of the substance in the aqueous solution. In particular aspects, the temperature change substance is a particle that has a substantial energy difference between a dissolved state and a crystalline state, so that energy in the form of heat is absorbed or released to the environment upon contact with urine. In other aspects, the temperature change substance releases or absorbs energy during swelling or reacting of the substance in an aqueous solution.

While a wide variety of substances may result in a temperature change when contacted with an aqueous solution, the selection of a particular temperature change substance and the determination of the amount to be used should be based in part on the desired temperature change. Specifically, the absorbent article 10 desirably provides a surface temperature change when wet of from about 5 to about 25° F. (2.8°-13.8° C.). To achieve this result, the temperature change substance, the amount used, and the location of the substance should be selected so that the possible total energy change is from about 6 to about 30 calories per square centimeter (cal/cm$^2$), which may represent either a possible total energy release of from about 6 to about 30 cal/cm$^2$ or a possible total energy absorption of from about 6 to about 30 cal/cm$^2$. More desirably, the temperature change substance, the amount used, and the location of the substance should be selected so that the possible total energy change is from about 12 to about 24 cal/cm$^2$, and more particularly about 18 cal/cm$^2$.

By way of example, urea particles may be selected to provide a cooling sensation, because urea particles absorb heat when dissolved in an aqueous solution. Urea has a heat of solution of approximately −60 calories per gram (cal/g). A desirable add-on amount for the urea particles would be a basis weight of about 0.3 grams per square centimeter (g/cm$^2$). The selection of urea particles at this basis weight results in a possible total energy change of 60 cal/g×0.3 g/cm$^2$ which equals 18 cal/cm$^2$.

Temperature change substances that absorb or release heat on contact with an aqueous solution desirably have a heat of solution, hydration, or reaction greater than about 40 cal/g or less than about −40 cal/g. The heat of solution, hydration, or reaction is suitably within the range of from about 40 to about 90 cal/g or from about −40 to about −90 cal/g, and more particularly from about 50 to about 70 cal/g or from about −50 to about −70 cal/g, such as urea at −60 cal/g. Suitable basis weights for such temperature change substances 70 range from about 0.1 to about 0.5 g/cm$^2$, and more particularly from about 0.2 to about 0.4 g/cm$^2$.

As referenced above, temperature change substances suitable for use in the absorbent article 10 include those that dissolve in an aqueous solution. The solubility of such temperature change substances is desirably from about 0.1 to about 3 grams of water (H$_2$O) per gram of material (g/g), and more particularly from about 0.1 to about 2 g/g for improved performance.

Suitable temperature change substances that absorb heat during dissolution can include salt hydrates, such as sodium acetate (H$_2$O), sodium carbonate (10H$_2$O), sodium sulfate (10H$_2$O), sodium thiosulfate (5H$_2$O), and sodium phosphate (10H$_2$O); anhydrous salts, such as ammonium nitrate, potassium nitrate, ammonium chloride, potassium chloride, and sodium nitrate; organic compounds, such as urea, xylitol, and other sugars; or the like. Temperature change substances that release heat during dissolution can include aluminum chloride, aluminum sulfate, potassium aluminum sulfate, or the like. The temperature change substance may also include those substances that absorb or release heat during swelling. By way of illustration, one suitable temperature change particle that releases heat during swelling is a lightly cross-linked partially neutralized polyacrylic acid.

Alternatively, the temperature change substance may include those substances that absorb or release heat upon reaction with an aqueous solution. Examples include ortho esters or ketals such as menthone ketals that result from reacting menthone with alcohols containing 1 to 8 carbons or polyols containing 2 to 8 carbons, and all structural and optical isomers thereof. Particular menthone ketals that may be suitable include menthone-glycerol ketal and menthone-propylene glycol ketal. Particular ketals are disclosed in U.S. Pat. No. 5,348,750 issued Sep. 20, 1994, to Greenberg; and in U.S. Pat. No. 5,266,592 issued Nov. 30, 1993, to Grub et al.; the contents of which are incorporated herein by reference to the extent that they are consistent (i.e., not in conflict) herewith.

The temperature change substance is desirably, although not necessarily, in the form of particles 21 sandwiched between the first and second containment layers 22. The first containment layer 22 may, for example, include a porous film or fibrous layer. The fibrous layer may include a fibrous tissue, a woven or nonwoven fabric, a cellulosic fibrous web, or the like. In one aspect, for example, the first containment layer 22 can include a cellulosic tissue composed of a conventional forming tissue having a basis weight of about 16.6 gsm and manufactured by a continuous wet press (CWP) process from a furnish composed of 100% LL-19 Northern Softwood Kraft (NSWK) fiber. The LL-19 fiber can be obtained from Kimberly-Clark Forest Products, Inc., Terrace Bay, Ontario, Canada. The forming tissue has a Frazier Porosity of about 50-350 cfm/ft$^2$ (cubic-feet-per minute per square foot).

The second containment layer 22 may, for example, include a liquid-permeable web material, such as a liquid-permeable film, tissue, fabric, or the like. The fabric may be woven or nonwoven, and may be composed of a hydrophilic material or composed of a hydrophobic material which has been suitably treated to render it sufficiently hydrophilic. In one aspect, the second containment layer 22 includes a conventional barrier tissue having a basis weight of about 21.2 gsm and manufactured by a CWP machine process from a furnish composed of 50%/50% Hinton EF (Softwood) and LL-16 Northern Hardwood Kraft (NHWK) fiber. The Hinton EF fiber can be obtained from Weldwood, a division of Canada, Ltd., Hinton, Alberta, Canada; and the LL-16 fiber can be obtained from Kimberly-Clark Forest Products, Inc., Terrace Bay, Ontario, Canada. The barrier tissue can have a Frazier Porosity of about 80-120 $cfm/ft^2$;

The leakage warning element 20 desirably provides a surface temperature change when wet of from about 5 to about 25 degrees Fahrenheit (° F.) (2.8°-13.8° C.) at the surface of the liner 64. Surface temperature changes within this range are believed to be identifiable to most absorbent article wearers. More desirably, the training pant 12 provides a surface temperature change when wet of from about 10° to about 20° F. (5.5°-11.1° C.), and particularly about 15° F. (8.3° C.) for improved performance. Also, the cool or warm sensation produced by the leakage warning element 20 should last from about 1 to about 120 seconds, and particularly from about 10 to about 60 seconds, such as about 30 seconds.

In an alternative aspect of the disclosure, the temperature change particles 21 are desirably accumulated in a plurality of pockets. Without wishing to be bound by any particular theory, positioning the temperature change particles 21 in discrete pockets is thought to enhance performance because the particles 21 in the interior portions of the pockets are, for an extended period of time, damp rather than saturated. As a result, the heat taken in or released by these temperature change particles 21 as they enter solution, swell, or react comes from the surrounding environment rather than solely from the urine or other body exudates.

Consequently, locating the temperature change particles 21 in pockets within the leakage warning element 20 facilitates generation of a cool or a warm sensation in an efficient and cost effective manner.

In another aspect of the disclosure illustrated in FIG. 3, the leakage warning element 20 is adapted to provide the wearer with an expanding or contraction dimensional change sensation. Dimensional change elements of this type are described in more detail in U.S. Pat. No. 5,649,914 to Glaug et al., the contents of which are incorporated herein by reference to the extent that they are consistent (i.e., not in conflict) herewith. The leakage warning element 20 includes a dimensional change member 28 positioned within the containment layers 22. The peripheries of the containment layers 22 may be bonded directly together by adhesives, thermal bonds, ultrasonic bonds, or other suitable means.

The dimensional change member 28 includes a material or materials that rapidly undergo a change in at least one dimension when exposed to an aqueous solution. The dimensional change is suitably either as an expansion to at least about 2 times a dry dimension or as a contraction to less than about one-half (½) of the dry dimension. In particular aspects, the dimensional change is either an expansion to at least about 5 times the dry dimension or a contraction to less than about one-fifth (⅕) of the dry dimension. For example, the dimensional change member 28 has a wet height dimension that is at least about 5 times greater than its dry height dimension, and more desirably at least about 10 times greater for improved performance. The height dimension of the dimensional change member 28 is perpendicular to the plane formed by the longitudinal and transverse axes 40, 42 of the absorbent article 10 so that the dimensional change is noticeable to the wearer of the absorbent article 10. The other dimensions, the width and length, of the dimensional change member 22 may remain the same, expand, or contract when exposed to an aqueous solution.

In one particular aspect, the dimensional change member 28 includes a compressed cellulose sponge having a dry height of about 0.9 mm and a wet height of about 9.5 mm. The height dimensions are measured with the material under a compressive load of 0.2 pounds per square inch.

The noncompressed axes of the material, that is the width and length, expand only about 7 percent from dry to wet states. Additionally, the dimensional change member 28 is desirably generally hydrophobic so that the dimensional change member 28 releases liquid to the absorbent article 10.

In one aspect of the disclosure, the dimensional change member 28 is capable of expanding to at least about 5 times its dry height in 10 seconds, and more particularly to at least about 10 times its dry height in 3 seconds for improved performance.

Suitable materials for use in the dimensional change member 28 include expandable foams, compressed cellulose sponges, superabsorbents, or the like. Particularly, desirable expandable foams include those having open, large cell, reticulated structures. Examples of such expandable foams are available from O-Cell-O, General Mills, Inc., Tonawanda, N.Y., USA, and Industrial Commercial Supply Co., Akron, Ohio, USA. The material forming the dimensional change member 28 may be softened by mechanical means or other suitable techniques so as to be less noticeable until urination occurs. One such means that is effective with compressed cellulose sponge is to run the material through a set of meshed gears with the gap between the gears set so that the material is sufficiently scored to make it pliable.

In another aspect of the present disclosure illustrated in FIGS. 3 and 4, the dimensional change member 28 may be a urine-or-other-body-exudates-permeable inflatable container 24 positioned between the bodyside liner 64 and the absorbent assembly 60. Dimensional change elements of this type are described in more detail in U.S. Pat. No. 7,002,055 to Long et al., the contents of which are incorporated herein by reference to the extent that they are consistent (i.e., not in conflict) herewith. The inflatable container 24 includes a surfactant and a system that, upon wetting with urine or other body exudates, produces a gas, such as carbon dioxide. The gas produced upon wetting with urine or other body exudates interacts with the surfactant to produce a foam that inflates the container 24. The inflated container 24 pushes against the bodyside liner and causes the bodyside liner to press against the skin of the wearer to alert the wearer that the absorbent assembly 60 is nearing fullness.

The inflatable container 24 that is positioned between the bodyside liner 64 and the absorbent assembly 60 includes an inflatable liquid permeable container 24. The container 24 may be suitably formed from either woven or nonwoven substrates that are substantially liquid permeable to allow liquids, such as urine, to pass therethrough and contact the gas producing system and surfactant described herein. In one aspect, the inflatable liquid permeable container 24 may be formed from a 20 gsm spunbond nonwoven material available from Kimberly-Clark Corporation, Neenah, Wis., U.S.A. More particularly, a pair of opposed sheets of such material may be ultrasonically or otherwise bonded together along an edge margin about the periphery of the container 24 so as to seal the container 24. The container 24 may be either adhesively or thermally bonded to the absorbent assembly 60 and/or the bodyside liner 64 to stabilize the container 24 during use. The container 24 is sized, configured, and positioned in the absorbent article 10 in such a manner that the container 24 is free to swell without substantial interference from other components of the absorbent article 10.

It should be understood that the container 24 could be fabricated from materials other than a spunbond nonwoven so long as at least a portion of the container 24 is sufficiently liquid permeable to permit liquid body exudates to permeate therethrough into the interior of the container 24 for contact with the gas producing systems and surfactants described herein.

As noted above, the permeable inflatable container 24 includes a system capable of generating a gas upon being wetted. The gas that is produced in the container 24 upon the wetting interacts with one or more surfactants, which are discussed below, and produces foam that inflates the container 24 and causes it to press the bodyside liner 64 against the skin of the wearer to alert the wearer that the absorbent assembly 60 is nearing fullness. FIG. 4 shows an absorbent assembly 60, a bodyside liner 64, and a permeable inflatable container 24, which is filled with foam. As shown in FIG. 4, the inflated container 24 pushes against the bodyside liner 64 and distorts the bodyside liner 64. The distortion causes the bodyside liner 64 to press against the skin of the wearer to alert the wearer the nearing fullness of the absorbent assembly 60.

In one aspect, the system capable of generating gas upon being wetted, which is located in the permeable inflatable container 24, includes at least one acid and at least one base. The acid and base react together upon being wetted to produce a gas that may be, for example, carbon dioxide gas. The exact gas produced by the gas producing system is not critical, so long as the gas produced is substantially non-harmful to the skin of the wearer.

In another aspect, the system capable of generating a gas upon being wetted includes a urine-or-other-body-exudates-soluble effervescent solid material produced in such a manner such that a pressurized gas is trapped within cells located in the solid material. When the solid material having pressurized gas-containing cells is contacted with urine or other body exudates, the solid material begins to dissolve and the pressurized gas is released from the cells during dissolution of the solid material. This gas can interact with the surfactant, also located in the permeable inflatable container 24, and produce a foam and bubbles that inflate the container 24 as described herein.

In this aspect, the soluble effervescent solid material may include a sugar compound such as a mono-saccharide, di-saccharide, or poly-saccharide that has been infused with a gas that is substantially non-reactive with human skin. Suitable gases for infusion into a solid material include, for example, carbon dioxide, air, nitrogen, argon, helium, other substantially inert gases, and combinations thereof. Specific examples of saccharides that can be used in accordance with the present disclosure include glucose, fructose, sucrose, lactose, maltose, dextrin, cyclodextrin, and the like, alone or in combination. Also, a mixture of sucrose with corn syrup (containing glucose, maltose, and dextrin) can be used in accordance with this aspect of the present disclosure to produce a gas-containing effervescent agent. Other examples of compounds that are capable of being prepared in such a manner as to trap pressurized gas in cells include, for example, water soluble compounds such as salts, alkali halides, and alkaline earth metal halides. Specific salts useful in the present disclosure include, for example, sodium chloride, potassium chloride, potassium bromide, lithium chloride, cesium chloride, and the like. Typically, the cells containing the pressurized gas have a diameter of from about 5 micrometers to about 100 micrometers.

The substantially non-reactive gas can be infused into the cells of the soluble solid material to produce an effervescent agent useful in the present disclosure by first heating the starting material, such as a sugar, in a small amount of water until the material is dissolved. After dissolution of the material, the water is evaporated off leaving the material in a molten state. The molten material is then gasified by introducing a suitable gas, such as carbon dioxide, at a superatmospheric pressure into a sealed vessel containing the molten material. The molten material is agitated during gasification to ensure intimate contact between the molten material and the gas. Pressures of, for example, between about 50 psig (340 kPa) and about 1000 psig (6890 kPa) may be utilized to infuse the gas into the molten material. After gas infusion, the molten material is allowed to solidify while maintained in the sealed vessel to produce an effervescent agent. A suitable procedure of producing a gas-containing solid material is fully set forth in U.S. Pat. No. 4,289,794 issued to Kleiner et al., the contents of which are incorporated herein by reference to the extent that they are consistent (i.e., not in conflict) herewith. The above procedure can produce solid effervescent agents containing cells of pressurized gas from about 50 psig (340 kPa) to about 900 psig (6200 kPa) which, when exposed to urine or other body exudates, allow the release of the trapped gas. This trapped gas, when released, can interact with the surfactant material in the container 24 described herein. The container 24 may suitably include from about 0.1 grams to about 15 grams of effervescent solid material containing a pressurized gas.

As noted above, the container 24 additionally includes a surfactant. The surfactant component located in the permeable inflatable container 24 is present as a foaming agent. When a gas, such as carbon dioxide, is produced from the gas generating system located in the container 24, the gas interacts with the surfactant and a bubble-filled foam is produced. These bubbles inflate the container 24 and cause it to swell and push against the bodyside liner 64 which, in turn, pushes against the skin of the wearer to alert the wearer to the nearing fullness of the absorbent assembly 60.

The surfactant used is not critical so long, as it does not substantially irritate the skin upon contact. A wide variety of surfactants may be suitable for use in accordance with the present disclosure. For example, suitable surfactants include anionic surfactants, nonionic surfactants, amphoteric surfactants, cationic surfactants, and combinations thereof. Examples of suitable anionic surfactants include alkyl benzene sulfonates, alkyl sulfates, alkyl ether sulfates, sulfosuccinates, and combinations thereof. Examples of suitable nonionic surfactants include ethoxylated alcohols, fatty acid alkanolamides, ethoxylated alkanolamides, amine oxides, and combinations thereof. Examples of suitable amphoteric surfactants include alkyl betaines, amidobetaines, and combinations thereof. Examples of suitable cationic surfactants include alkylammonium halides. Generally, the container 24 will include from about 0.1 grams to about 15 grams of surfactant.

In one aspect of the present disclosure, the components included in the system capable of generating a gas, such as carbon dioxide, upon being wetted and/or the surfactant present in the permeable inflatable container 24 may be encapsulated in a urine-or-other-body-exudates-soluble shell material prior to introduction into the container 24. For example, if the system capable of generating a gas upon being wetted includes an acid and a base, the acid and the base may be separately encapsulated in a soluble encapsulation material to keep the components separated until wetted. Alternatively, the acid and base components may be encapsulated together if reactivity between the acid and the base in the absence of a liquid is not a concern. The surfactant may be separately encapsulated, or may be encapsulated with the acid and/or the base. Additionally, encapsulation may be used with gas-impregnated effervescent agents alone or in combination with the surfactant.

The shell material used for encapsulation may be suitably constructed of a material such that it will release the encapsulated material (i.e., the acid, base, effervescent agent and/or surfactant) upon contact with urine or other body exudates. The urine or other body exudates may cause the shell material to solubilize, disperse, swell, or disintegrate, or the shell material may be permeable such that it disintegrates or discharges the encapsulated material upon contact with urine or other body exudates. Suitable shell materials include cellulose-based polymeric materials (e.g., ethyl cellulose), carbohydrate-based materials (e.g., starches and sugars) and materials derived therefrom (e.g., dextrins and cyclodextrins) as well as other materials compatible with human tissues.

The shell thickness may vary depending upon the material encapsulated, and is generally manufactured to allow the encapsulated component to be covered by a thin layer of encapsulation material, which may be a monolayer or thicker laminate, or may be a composite layer. The layer should be thick enough to resist cracking or breaking of the shell during handling or shipping of the product or during wear which would result in breakage of the encapsulating material. The material should also be constructed such that humidity from atmospheric conditions during storage, shipment, or wear will not cause a breakdown of the microencapsulation layer.

In another aspect of the present disclosure, a system similar to the pressure container 24 described above may be used. Applying the appropriate substance(s) directly to or within the bodyside liner 64, absorbent assembly 60, or surge layer will result in a foaming or fizzing physical sensation upon insult with urine or other body exudates. In essence, the substances described above for use with an inflating container 24 may be used without the container 24 to produce a foaming or fizzing sensation directly to the wearer's skin. The substances are formed with or applied to the bodyside liner 64, absorbent assembly 60, or surge layer of the absorbent article 10.

For example, the one or more of the substances described above could be combined in an air laid material or in a coform material and incorporated into the absorbent article 10. As a specific example, tartaric acid can be combined with a coform on one layer with calcium carbonate on that or another layer. This material will then bubble vigorously when subjected to an aqueous solution. That bubbling is detectable to the wearer of the absorbent article 10 and signals that the absorbent assembly 60 is nearing fullness.

Adult Undergarments

Figure 5:
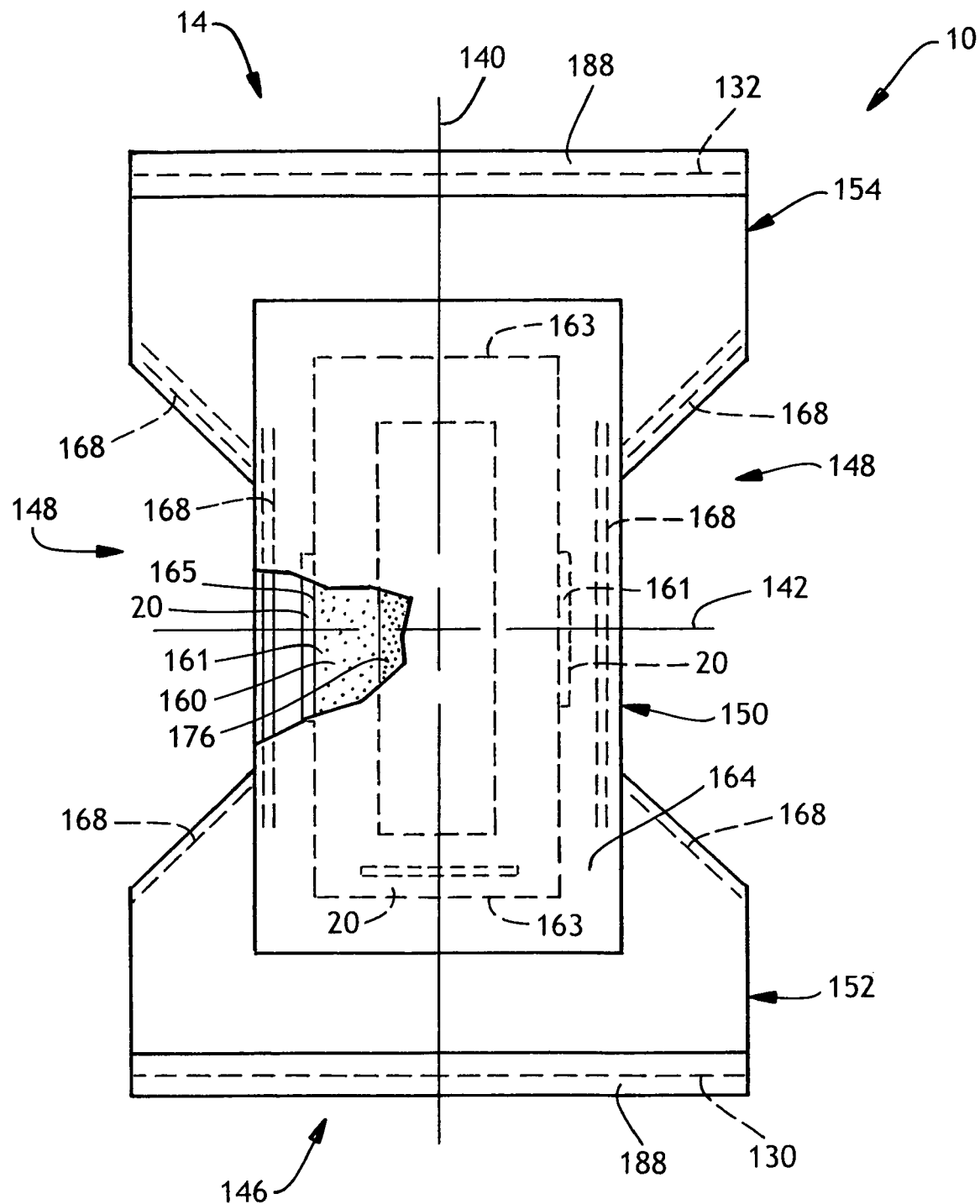
FIG. 5 representatively illustrates a plan view of a particular aspect of an adult garment of the present disclosure.

Referring to FIG. 5, a disposable pant-like absorbent adult undergarment 14 is depicted. The undergarment 14 is designed to be pulled up around a wearer's torso without having to first open the undergarment 14 to place it on a wearer's body. In FIG. 5, the undergarment 14 is shown as it would appear after it has been removed from the package but before it is pulled up around a wearer's torso.

The undergarment 14 has a longitudinal axis 140 and a transverse axis 142. The undergarment 14 includes a front waist region 152, a back waist region 154 and a crotch region 150. The crotch region 150 joins the front waist region 152 to the back waist region 154. The front and back regions 152 and 154 can be stretchable. By "stretchable" it is meant that the regions 152 and 154 can be increased in size, for example lengthened, widened or extended in one or more dimensions by applying a force, such as by pulling. The crotch region 150 can be stretchable or non-stretchable but desirably is non-stretchable.

The front waist region 152 has a front end edge 130 and the back waist region 154 has a back end edge 132. The undergarment 14 can be folded approximately along the transverse axis 142 such that the front end edge 130 aligns with the back end edge 132.

The front waist region 152 and the back waist region 154 are shown as being separate and discontinuous from one another although the front, back and crotch regions 152, 154, and 150 could be formed from a single piece of material, if desired. Desirably, the front waist region 152 is formed from a similar or identical material as the back waist region 154. The undergarment 14 has a bodyside liner 164 and an outercover (not shown). The bodyside liner 164 will be in direct contact with the wearer's skin when the undergarment 14 is worn. The outercover or garment-facing surface will be spaced away from the wearer's skin and will be adjacent to any outer clothing that the wearer may be wearing.

The front and back waist regions 152 and 154 can be constructed from various materials. The material can be a single layer or be a laminate of two or more layers. Spunbond is a material that works well for the front and back waist regions 152 and 154. Spunbond is a nonwoven material that is capable of being stretched at least a minimum amount. Spunbond is manufactured and sold by Kimberly-Clark Corporation having an office at 401 North Lake Street, Neenah, Wis. 54956, U.S.A. Any other suitable material can also be used.

Other options for the front and back waist regions 152 and 154 can include two outer layers having a plurality of elastic strands sandwiched therebetween. The elastic strands can be formed from LYCRA brand elastic available from E. I. DuPont de Nemours & Company of Wilmington, Del., U.S.A.

The undergarment 14 also includes an absorbent assembly 160 present in the crotch region 150. The absorbent assembly 160 can include a liquid pervious bodyside cover, a liquid-impervious backsheet, and an absorbent positioned therebetween. The absorbent in the absorbent assembly 160 can be formed from natural or synthetic materials. The absorbent can be made from cellulosic fibers, wood pulp, textile fibers or from other absorbent materials known to those skilled in the art. Superabsorbents, commonly in solid form and in the shape of small particles, granules, flakes, etc., can be mixed, combined, attached, printed or otherwise added to the absorbent material to increase the absorbent capacity of the absorbent. A surge layer 176 can also be optionally used, which is normally positioned between the bodyside liner 164 and the absorbent assembly 160. The surge layer 176 can function to rapidly acquire and temporarily retain body fluid, such as urine, before it can be absorbed into the absorbent. Desirably, the surge layer 176 is also capable of wicking body fluid lengthwise and/or widthwise across its surface as well as directing the body fluid downward in a z-direction, toward the absorbent.

The undergarment 14 further includes a waistband 188 secured to the front and back end edges 130 and 132. A portion of the waistband 188 overlaps each of the front and back waist regions 152 and 154 and projects outward therefrom. The waistband 188 can be described as extending outward from the front and back end edges 130 and 132 in a cantilevered configuration.

The waistband 188 can be constructed from almost any elastic material having stretch and retraction capabilities. A desirable nonwoven material from which the waistband 188 can be constructed is spunbond. The waistband 188 can be a laminate containing a first layer, a second layer and two or more elastic strands positioned therebetween. The outer two layers can be constructed or formed from a woven or a nonwoven material, a natural or synthetic material, an elastic film, a thermoplastic film, or from any other material known to those skilled in the art. The number of elastic strands positioned between the two outer layers can vary depending upon the width of the waistband 188. The elastic strands can be formed from LYCRA brand elastic available from E. I. DuPont de Nemours & Company of Wilmington, Del. U.S.A.

The undergarment 14 further includes a pair of side seams (not shown) which function to join, bond and/or secure the front waist region 152 to the back waist region 154. The pair of side seams extend through the waistband 188 as well to form a unitary undergarment. By "unitary" it is meant that the undergarment 14 is designed to be stepped into by a wearer and the undergarment 14 is then pulled up along the wearer's legs and thighs and positioned around the wearer's torso. There is no need to first open a unitary undergarment before it is applied to a wearer's body. The unitary undergarment 14 has a longitudinal axis 140, a waist opening 146, and a pair of leg openings 148.

The undergarment 14 further includes leg elastic members 168, each of which at least partially surrounds the pair of leg openings 148. The elastic members 168 can consist of one or more elastic strands. Each of the elastic members 168 can be formed as a continuous or a non-continuous member. In FIG. 5, each of the elastic members 168 is depicted as two separate and distinct members that are spaced apart from one another. However, a single elastic member 168, consisting of two or three elastic strands, could be employed that extend from one side seam to the opposite side seam.

The undergarment 14 may also include leg cuffs or leg flaps, each of which at least partially surrounds the pair of leg openings 148, to better seal the leg openings 148 against leakage (not shown). The leg cuffs can also include elastic members consisting of one or more elastic strands. Each of the elastic members can be formed as a continuous or a non-continuous member.

The absorbent assembly 160 can be in a variety of shapes and configurations as are known in the art, such as rectangular, hourglass shaped, I-shaped, and the like. The absorbent assembly 160 has opposed lateral edges 161 and opposed longitudinal ends 163. The lateral edges 161 and longitudinal ends 163 together make up the perimeter 165 of the absorbent assembly 60.

The leakage warning element 20 is positioned within the adult garment 14 so that urine or other body exudates filling the absorbent assembly 160 contacts the leakage warning element 20 prior to completely filling and eventually leaking from the adult garment 14. Thus, the leakage warning element 20 is disposed with or near the absorbent assembly 160 so that urine or other body exudates contacting the absorbent assembly will also eventually contact the leakage warning element 20. Most desirably, the leakage warning element 20 is disposed on the bodyside of the absorbent assembly 160 so as to be sandwiched between the absorbent assembly 160 and the bodyside liner 164. In this way, the physical sensation resulting from the leakage warning element 20 is more easily noticed by the wearer.

Alternatively, however, the leakage warning element 20 may be located within the absorbent assembly 160 or beneath the absorbent assembly 160 (not shown). The leakage warning element 20 can also be positioned on the leg cuffs or containment flaps or in any other suitable position in the adult garment 14, as long as fluid communication is provided between the absorbent assembly 160 and the leakage warning element 20. Leakage warning elements 20 can be positioned on the flaps, positioned as a single web at the center of the flaps, slit with the flaps, or placed at the flap base. The leakage warning element 20 can also be placed near the flap elastic members so that the substances are encapsulated in the flap material, not allowing the particle material to fall out. In addition, leakage warning elements 20 may be positioned in more than one location within the adult garment 14. The leakage warning element 20 may be bonded in position using adhesives, ultrasonic bonds, or other suitable means.

One or more leakage warning elements 20 may be disposed in the adult garment 14. As illustrated in FIG. 5, a pair of leakage warning elements 20 is positioned on opposite sides of the longitudinal axis 140 and spaced apart from the intersection of the longitudinal and transverse axes 140, 142 along the transverse axis 142. Similarly, a pair of leakage warning elements 20 may be positioned on opposite sides of the transverse axis 142 and spaced apart from the intersection of the longitudinal and transverse axes 140, 142 along the longitudinal axis 140 (not shown). In another aspect, leakage warning elements 20 may be positioned at each of the points at which an axis meets the perimeter 165 of the absorbent assembly 160 (not shown). In still another aspect, the leakage warning elements 20 may be positioned completely or partially along the entire absorbent assembly perimeter 165 (not shown).

The position and/or structure of the leakage warning elements 20 should be such that the leakage warning elements 20 come in contact with urine or other bodily waste as the absorbent assembly 160 fills but prior to any leakage from the absorbent assembly 160. The leakage warning elements 20 may be centered in the longitudinal direction 140. Alternatively, however, the leakage warning elements 20 may be located off the transverse axis 140 of the adult garment 14 (not shown). Likewise, the leakage warning elements 20 may be centered in the transverse direction 142 or may be located off the longitudinal axis 142 of the adult garment 14 (not shown).

Figure 6:
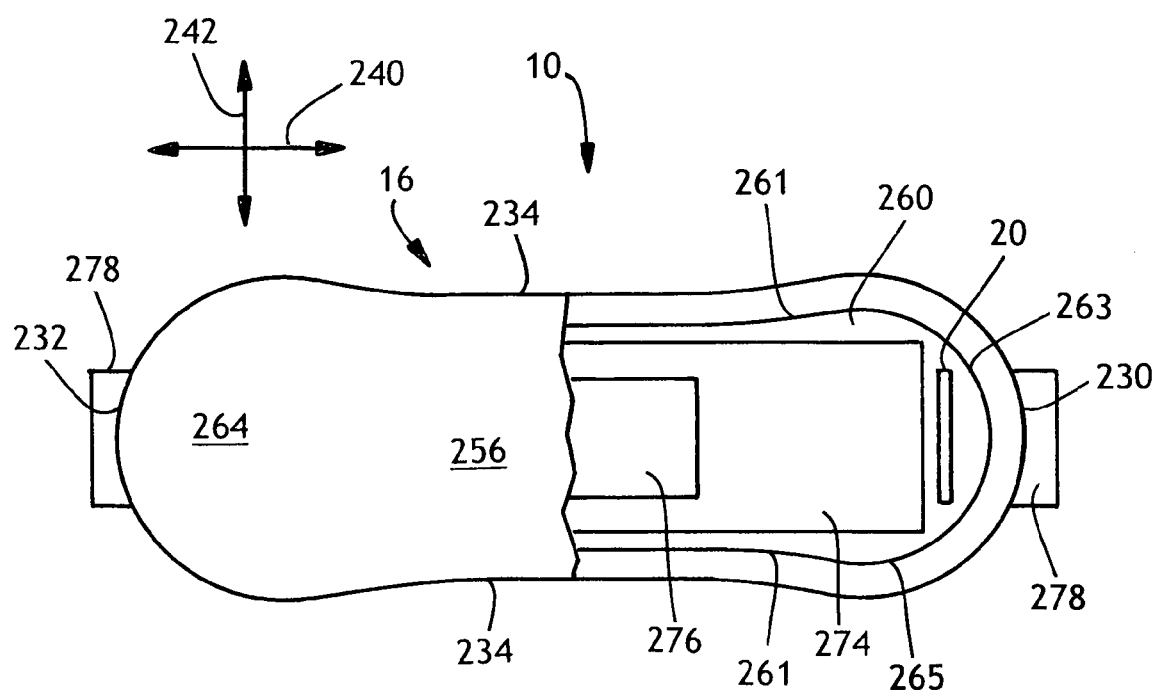
FIG. 6 representatively illustrates a plan view of a feminine/incontinence pad of the present disclosure showing the surface of the feminine/incontinence pad that faces the wearer when worn, and with portions cut away to show underlying features.
Figure 7:
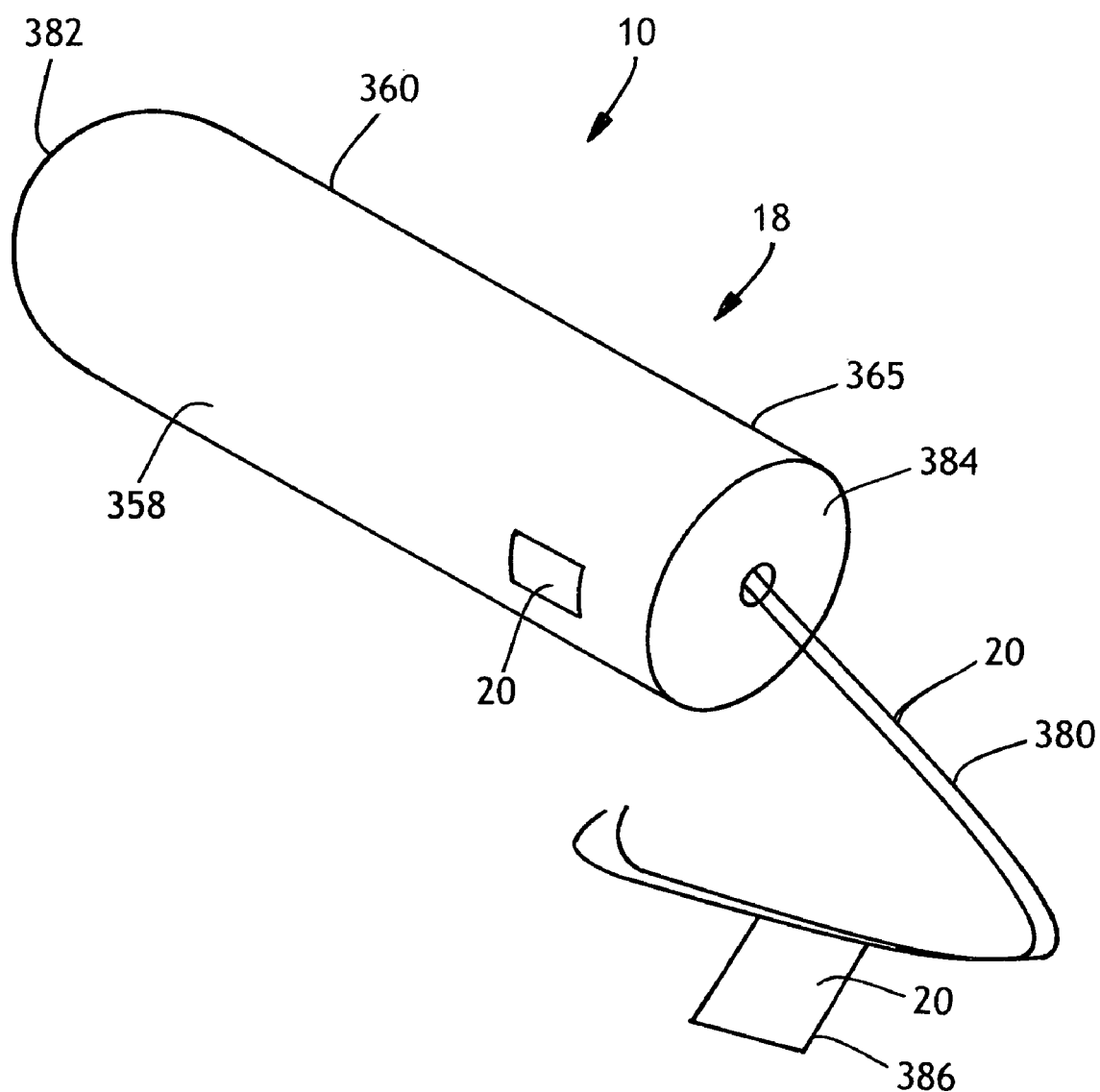
FIG. 7 representatively illustrates a perspective view of a number of aspects of a tampon of the present disclosure.

In a similar manner, the present disclosure may be applied to a feminine/incontinence pad 16 as well, as illustrated in FIG. 6. The exemplary feminine/incontinence pad 16 includes an outercover (otherwise referred to as a baffle or backsheet, not shown), an absorbent assembly 260, an optional tissue layer 274, an optional distribution layer (surge layer) 276 and a bodyside liner 264 (also referred to as the topsheet). The feminine/incontinence pad 16 also has first and second side edges 234 that are the longitudinal sides of the elongated feminine/incontinence pad 16. The side edges 234 can be contoured, for example, in a concave shape, or they can be linear. The sides can further include flaps (not shown) that extend laterally outward. Flaps are known in the art and are shown in, for example U.S. Pat. No. 6,387,084 issued to VanGompel et al., the contents of which are incorporated herein by reference to the extent that they are consistent (i.e., not in conflict) herewith. In one embodiment (not shown), one or more elastic elements are disposed along the sides to form a gasket with the body of the wearer. Elastic sides are known in the art, as is shown in U.S. Pat. No. 6,315,765 issued to Datta et al., the contents of which are incorporated herein by reference to the extent that they are consistent (i.e., not in conflict) herewith. In one embodiment, the elastic elements are disposed between the bodyside liner 264 and the outercover.

The feminine/incontinence pad 16 has a bodyside inner surface 256 and a garment-side outer surface. Applied to at least a portion of the garment-side outer surface is a garment attachment adhesive. In various embodiments, the garment attachment adhesive is configured as a single band of adhesive or as two or more spaced apart strips. Alternatively, the garment attachment adhesive may include a swirl pattern of adhesive which encompasses a major portion of the garment-side outer surface of the feminine/incontinence pad 16.

A release strip 278, also known as a releasable peel strip, is removably secured to the garment attachment adhesive and serves to prevent premature contamination of the adhesive before the feminine/incontinence pad 16 is secured to the crotch portion of an undergarment. In various embodiments, the garment attachment adhesive is designed to be secured to the inner crotch portion of an undergarment so as to keep the absorbent product in register with the body of the wearer. The release strip 278 may extend beyond one or both of the end edges 230, 232 of the outercover, as shown in FIG. 1. Alternatively, the release strip 278 may be as short as the length of the garment attachment adhesive, or slightly longer than the adhesive or may be only as long as the garment attachment adhesive, but does not extend beyond the end edges 230, 232 of the outercover.

The body-side liner or topsheet 264, which is preferably liquid permeable, may be formed from one or more materials. The body-side liner or topsheet 264 must be able to manage different body excretions depending on the type of product. In feminine care products, often the body-side liner or body-contacting layer 264 must be able to handle menses and urine. In the present disclosure, the body-side liner or topsheet 264 may include a layer constructed of any operative material, and may be a composite material. For example, the body-side liner or body-contacting layer 264 can include a woven fabric, a nonwoven fabric, a polymer film, a film-nonwoven fabric laminate or the like, as well as combinations thereof. Examples of a nonwoven fabric useable in the body-side liner or topsheet 264 include, for example, an airlaid nonwoven web, a spunbond nonwoven web, a meltblown nonwoven web, a bonded-carded-web, a hydroentangled nonwoven web, a spunlace web or the like, as well as combinations thereof. Other examples of suitable materials for constructing the body-side liner or topsheet 264 can include rayon, bonded-carded-webs of polyester, polypropylene, polyethylene, nylon, or other heat-bondable fibers finely perforated film webs, net-like materials, and the like, as well as combinations thereof. These webs can be prepared from polymeric materials such as, for example, polyolefins, such as polypropylene and polyethylene and copolymers thereof, polyesters in general including aliphatic esters such as polylactic acid, nylon or any other heat-bondable materials.

Other examples of suitable materials for the body-side liner or topsheet 264 are composite materials of a polymer and a nonwoven fabric material. The composite materials are typically in the form of integral sheets generally formed by the extrusion of a polymer onto a nonwoven web, such as a spunbond material. In a desired arrangement, the liner or body contacting layer 264 can be configured to be operatively liquid-permeable with regard to the liquids that the article is intended to absorb or otherwise handle. The operative liquid-permeability may, for example, be provided by a plurality of pores, perforations, apertures or other openings, as well as combinations thereof, which are present or formed in the liner or body contacting layer. The apertures or other openings can help increase the rate at which bodily liquids can move through the thickness of the liner or body contacting layer and penetrate into the other components of the article (e.g. into the absorbent assembly 260). The selected arrangement of liquid-permeability is desirably present at least on an operative portion of the body-side liner or topsheet 264 that is appointed for placement on the body-side of the article. The body-side liner or topsheet 264 can provide comfort and conformability, and can function to direct bodily exudates away from the body and toward the absorbent assembly 260. The body-side liner or topsheet 264 can be configured to retain little or no liquid in its structure, and can be configured to provide a relatively comfortable and non-irritating surface next to the body tissues of a wearer. In the present invention, the topsheet or body-facing surface of each absorbent article may be embossed, printed or otherwise imparted with a pattern.

The outercover may include a layer constructed of any operative material, and may or may not have a selected level of liquid-permeability or liquid-impermeability, as desired. In a particular configuration, the outercover may be configured to provide an operatively liquid-impermeable baffle structure. The outercover may, for example, include a polymeric film, a woven fabric, a nonwoven fabric or the like, as well as combinations or composites thereof. For example, the outercover may include a polymer film laminated to a woven or nonwoven fabric. In a particular feature, the polymer film can be composed of polyethylene, polypropylene, polyester or the like, as well as combinations thereof. Additionally, the polymer film may be micro-embossed, have a printed design, have a printed message to the consumer, and/or may be at least partially colored. Suitably, the outercover can operatively permit a sufficient passage of air and moisture vapor out of the article, particularly out of an absorbent (e.g. storage or absorbent assembly 260) while blocking the passage of bodily liquids. An example of a suitable outercover material can include a breathable, microporous film, such as those described in, for example, U.S. Pat. No. 6,045,900 to McCormack et al.

Bicomponent films or other multi-component films can also be used, as well as woven and/or nonwoven fabrics which have been treated to render them operatively liquid-impermeable. Another suitable outercover material can include a closed cell polyolefin foam. For example, a closed-cell polyethylene foam may be employed.

The liquid permeable body-side liner 264 and the liquid-impermeable outercover may be peripherally sealed together to enclose the absorbent assembly 260 to form the feminine/incontinence pad 16. Alternatively, the body-side liner or topsheet 264 can be wrapped around both the absorbent assembly 260 and the outercover to form a wrapped pad. The body-side liner 264 and outercover, and other components of the feminine/incontinence pad 16, can be joined for example with adhesive bonds, sonic bonds, thermal bonds, pinning, stitching or any other attachment techniques known in the art, as well as combinations thereof.

The absorbent assembly 260 can be in a variety of shapes and configurations as are known in the art, such as rectangular, hourglass shaped, I-shaped, and the like. The absorbent assembly 260 has opposed lateral edges 261 and opposed longitudinal ends 263. The lateral edges 261 and longitudinal ends 263 together make up the perimeter 265 of the absorbent assembly 60.

The absorbent assembly 260 is designed to absorb body exudates, including menstrual fluid, blood, urine, and other body fluids. The absorbent assembly 260 may contain one or more layers of absorbent material. The layers can contain similar materials or different materials. Suitable materials for the absorbent assembly 260 include, for example, cellulose, wood pulp fluff, rayon, cotton, and meltblown polymers such as polyester, polypropylene or coform. Coform is a meltblown air-formed combination of meltblown polymers, such as polypropylene, and absorbent staple fibers, such as cellulose. A preferred material is wood pulp fluff, for it is low in cost, relatively easy to form, and has good absorbency.

The absorbent assembly 260 can also be formed from a composite including a hydrophilic material which may be formed from various natural or synthetic fibers, wood pulp fibers, regenerated cellulose or cotton fibers, or a blend of pulp and other fibers. A desired material is an airlaid material.

In one embodiment, the absorbent assembly 260 also includes a superabsorbent material, in addition to or in place of the hydrophilic material, which increases the ability of the absorbent core to absorb a large amount of fluid in relation to its own weight. Generally stated, the superabsorbent material can be a water-swellable, generally water-insoluble, hydrogel-forming polymeric absorbent material, which is capable of absorbing at least about 15, suitably about 30, and possibly about 60 times or more its weight in physiological saline (e.g. saline with 0.9 wt % NaCl). The superabsorbent materials can be inserted as particles or in sheet form. The superabsorbent material may be biodegradable or bipolar. The hydrogel-forming polymeric absorbent material may be formed from organic hydrogel-forming polymeric material, which may include natural material such as agar, pectin, and guar gum, modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers may be lightly crosslinked to render the material substantially water insoluble. Crosslinking may, for example, be by irradiation or covalent, ionic, Van der Waals, or hydrogen bonding. Hydroxyfunctional polymers have been found to be good superabsorbents for sanitary napkins. Such superabsorbents are commercially available from Dow Chemical, Hoechst-Celanese, and Stockhausen, Incorporated, among others, and are a partially neutralized salt of cross-linked copolymer of polyacrylic acid and polyvinyl alcohol having an absorbency under load value above 25 grams of absorbed liquid per gram of absorbent material (g/g). Other types of superabsorbent materials known to those skilled in the art can also be used.

Additional layers or substrates, including for example, the liquid acquisition and distribution layer 276, also referred to as a surge or transfer layer, and an optional tissue layer 274 can also be incorporated into the feminine/incontinence pad 16.

The leakage warning element 20 is positioned within the feminine/incontinence pad 16 so that urine or other body exudates filling the absorbent assembly 260 contacts the leakage warning element 20 prior to completely filling and eventually leaking from the feminine/incontinence pad 16. Thus, the leakage warning element 20 is disposed with or near the absorbent assembly 260 so that urine or other body exudates contacting the absorbent assembly will also eventually contact the leakage warning element 20. Most desirably, the leakage warning element 20 is disposed on the bodyside of the absorbent assembly 260 so as to be sandwiched between the absorbent assembly 260 and the bodyside liner 264. In this way, the physical sensation resulting from the leakage warning element 20 is more easily noticed by the wearer.

Alternatively, however, the leakage warning element 20 may be located within the absorbent assembly 260 or beneath the absorbent assembly 260 (not shown). The leakage warning element 20 can also be positioned on the flaps or in any other suitable position in the feminine/incontinence pad 16, as long as fluid communication is provided between the absorbent assembly 260 and the leakage warning element 20. In addition, leakage warning elements 20 may be positioned in more than one location within the feminine/incontinence pad 16. The leakage warning element 20 may be bonded in position using adhesives, ultrasonic bonds, or other suitable means.

One or more leakage warning elements 20 may be disposed in the feminine/incontinence pad 16. A pair of leakage warning elements 20 can be positioned on opposite sides of the longitudinal axis 240 and spaced apart from the intersection of the longitudinal and transverse axes 240, 242 along the transverse axis 242. Similarly, a pair of leakage warning elements 200 may be positioned on opposite sides of the transverse axis 242 and spaced apart from the intersection of the longitudinal and transverse axes 240, 242 along the longitudinal axis 240. In another aspect, leakage warning elements 20 may be positioned at each of the points at which an axis meets the perimeter 265 of the absorbent assembly 260. In still another aspect, the leakage warning elements 20 may be positioned completely or partially along the entire absorbent assembly perimeter 265.

The position and/or structure of the leakage warning elements 20 should be such that the leakage warning elements 20 come in contact with urine or other bodily waste as the absorbent assembly 260 fills, but prior to any leakage from the absorbent assembly 260. The leakage warning elements 20 may be centered in the longitudinal direction 240. Alternatively, however, the leakage warning elements 20 may be located off the transverse axis 240 of the feminine/incontinence pad 16. Likewise, the leakage warning elements 20 may be centered in the transverse direction 242 or may be located off the longitudinal axis 242 of the feminine/incontinence pad 16.

In a similar manner, the present disclosure may be applied to a tampon 18 as well. A tampon 18 is an absorbent article designed to be worn by a woman during her menstrual period to absorb menses and other body fluids. The tampon 10 includes an absorbent assembly in the form of a tampon body 360 and also includes a withdrawal string 380. The tampon body 360 is normally compressed into the form of a cylinder and may have a blunt, rounded or shaped forward end. The tampon body 360 has a forward or distal end 382 that is closer to the cervix when the tampon 18 is in use. The tampon body 360 also has a proximal or string end 384 that is closer to the vaginal opening when the tampon 18 is in use. The withdrawal string 380 is fastened to the tampon body 360 and typically extends from the proximal end 384. The withdrawal string 380 serves as a means for withdrawing the tampon 18 from the woman's vagina. Catamenial tampons 18 suitable for use in the present disclosure include an absorbent material as is known in the art. The distal end 382 of the tampon body 360 or the tampon body itself may be formed into specific shapes such as various cup shapes to enhance contact with the cervix, anterior formix, posterior formix, lateral formices, vaginal epithelium areas, or conformance to other anatomical areas within the vaginal or other cavity.

Tampons 18 may also leak, unbeknownst to the wearer, causing undesirable effects. Reasons for this leakage may include the shape of the tampon body 360 or the string 380, which, being absorbent, also can draw fluid out of the tampon body 360 causing leakage.

The tampon body 360 has an outer surface 358. The outer surface 358, the distal end 382, and the proximal end 384 together make up the perimeter 365 of the tampon body 360.

A leakage warning element 20 may be positioned in conjunction with a tampon 18. The specific placement of the leakage warning element 20 can be in a variety of places, including but not limited to the tampon string 380 or the proximal end 384 of the tampon body 360. Positioning the leakage warning element 20 on the string 380 provides less surface area that would potentially be in contact with the skin for alerting purposes, but would be an advantageous location for indication once a tampon 18 has begun to leak. Positioning the leakage warning element 20 at the proximal end 384 of the tampon body 360 would alert the wearer to the possibility that leakage may occur, and may also be an indication that the tampon 18 needs to be changed.

In one difference from those aspects described above, the leakage warning element 20 may be a temperature change substance coated on, impregnated into, or otherwise applied to the withdrawal string 380 of the tampon 18. The leakage warning element 20 may also be a tab or flag 386 constructed as described above and attached to the withdrawal string 380 at some point between the proximal end 384 of the tampon body 360 and the end of the string 380 away from the tampon body 360.

Aspects of the disclosure have been described with reference to various specific and illustrative aspects and techniques. However, it should be understood that many variations and modifications may be made while remaining within the spirit and scope. Accordingly, this is intended to embrace all such alternatives, modifications and variations that fall within the spirit and scope of the appended claims. As various changes could be made in the above constructions and methods, without departing from the scope of the disclosure, it is intended that all matter contained in the above description and shown in the accompanying drawings shall be interpreted as illustrative and not in a limiting sense.

When introducing elements of the disclosure or the preferred aspect(s) thereof, the articles "a", "an", "the" and "said" are intended to mean that there are one or more of the elements. The terms "comprising," "including," and "having" are intended to be inclusive and mean that there may be additional elements other than the listed elements.

What is claimed is:

1. An absorbent article for preventing leakage, the article comprising:
    an absorbent assembly having an absorbent assembly perimeter; and
    a leakage warning element disposed within the absorbent assembly and only adjacent a portion of the perimeter, wherein the leakage warning element is adapted to provide a physical sensation indicating a fullness level of the absorbent assembly.

2. The article of claim 1, wherein the absorbent assembly has a lateral edge, and wherein the portion of the perimeter is the lateral edge.

3. The article of claim 1, wherein the absorbent assembly has a longitudinal end, and wherein the portion of the perimeter is the longitudinal end.

4. The article of claim 1, the absorbent assembly has a longitudinal axis, and wherein the leakage warning element is spaced apart from the longitudinal axis.

5. The article of claim 1, the absorbent assembly has a transverse axis, and wherein the leakage warning element is spaced apart from the transverse axis.

6. The article of claim 1, wherein the leakage warning element is a temperature change element.

7. The article of claim 6, wherein the temperature change element is a cooling element.

8. The article of claim 7, wherein the cooling element includes a cooling material disposed on the absorbent assembly.

9. The article of claim 7, wherein the cooling element includes a cooling material disposed on a strip of material, and wherein the strip of material is disposed on the absorbent assembly.

10. The article of claim 7, wherein the cooling element includes a cooling material disposed on a strip of material, and wherein the strip of material is disposed adjacent a portion of the perimeter.

11. The article of claim 6, wherein the temperature change element is a heating element.

12. The article of claim 1, wherein the leakage warning element is a pressure-inducing element.

13. The article of claim 1, wherein the leakage warning element is a foam-producing element.

14. The article of claim 1, wherein the article is a tampon including a proximal end and a string attached at the proximal end.

15. The article of claim 14, wherein the portion of the perimeter is the proximal end.

16. The article of claim 14, wherein the portion of the perimeter is the string.

17. The article of claim 1, wherein the article is a garment-like article including leg openings, and wherein the leakage warning element is disposed adjacent the leg openings.

18. The article of claim 1, the article further including a flap, wherein the portion of the perimeter is the flap.

19. The article of claim 1, the article further including a cuff, wherein the portion of the perimeter is the cuff.

20. The article of claim 1, the article further including a tab, wherein the portion of the perimeter is the tab.

21. An absorbent article for providing a wearer with a warning of potential leakage, the article comprising:
    an absorbent assembly in fluid contact with a transport member; and
    a leakage warning element in fluid contact with the transport member such that the absorbent assembly is in fluid contact with the leakage warning element via the transport member, wherein the leakage warning element is adapted to impart a physical sensation to the wearer.

* * * * *